United States Patent [19]

Hidaka et al.

[11] Patent Number: 4,990,340

[45] Date of Patent: Feb. 5, 1991

[54] SUSTAINED RELEASE PHARMACEUTICAL PREPARATION

[75] Inventors: Osafumi Hidaka; Tomoki Sakai, both of Tokyo, Japan

[73] Assignee: Teijin Limited, Osaka, Japan

[21] Appl. No.: 522,493

[22] PCT Filed: Jan. 21, 1987

[86] PCT No.: PCT/JP87/00036

§ 371 Date: Sep. 22, 1987

§ 102(e) Date: Sep. 22, 1987

[87] PCT Pub. No.: WO87/44343

PCT Pub. Date: Jul. 30, 1987

Related U.S. Application Data

[63] Continuation of Ser. No. 110,760, Sep. 22, 1987, abandoned.

[30] Foreign Application Priority Data

Jan. 22, 1986 [JP] Japan ................................ 61-9844

[51] Int. Cl.$^5$ ............................................... A61F 13/00
[52] U.S. Cl. ..................................... 424/449; 424/444; 424/445; 424/447
[58] Field of Search ................ 424/445, 446, 447, 448, 424/449

[56] References Cited

U.S. PATENT DOCUMENTS 4,175,326 11/1979 Goodson ............................ 424/435
4,297,995 11/1981 Golub ................................ 128/156
4,713,243 12/1987 Schiraldi et al. .................. 424/435
4,764,377 8/1988 Goodson ........................... 424/435
4,801,458 1/1989 Hadaka et al. .................... 424/443

FOREIGN PATENT DOCUMENTS

| 0013606 | 7/1980 | European Pat. Off. . |
| 0113562 | 7/1984 | European Pat. Off. . |
| 0139127 | 5/1985 | European Pat. Off. . |
| 0168862 | 1/1986 | European Pat. Off. . |
| 2527450 | 2/1983 | France . |
| 56145215A | 3/1978 | Japan . |
| 5984815A | 7/1979 | Japan . |
| 57-31611A | 4/1981 | Japan . |

OTHER PUBLICATIONS

J. Lindhe et al., Journal of Clinical Periodontology 1979, pp. 141–149, "Local Tetracycline Delivery Using Hollow Fiber Device in Periodontal Therapy".

Patent Abstracts of Japan, vol. 11, No. 163, p. (C-424)[2610], May 26, 1987.

Primary Examiner—Merrell C. Cashion, Jr.
Assistant Examiner—Leon R. Horne
Attorney, Agent, or Firm—Sughrue, Mion, Zinn, Macpeak & Seas

[57] ABSTRACT

A sustained release pharmaceutical preparation for percutaenous administration use mainly composed of a drug layer which is a layer made to contain drugs, to have no adhesiveness to the skin, but to be used in contact with the skin.

3 Claims, 1 Drawing Sheet

SUSTAINED RELEASE PHARMACEUTICAL PREPARATION

This is a continuation of application Ser. No. 07/110,760 filed Sept. 22, 1988, now abandoned.

TECHNICAL FIELD

This invention relates to a sustained release pharmaceutical preparation for percutaneous administration use. More particularly, this invention relates to a sustained release pharmaceutical preparation for percutaneous administration use, with excellent effects of sustained release and minimized adverse reaction of the drug, being a pharmaceutical preparation mainly composed of a drug layer which is made to contain drugs, to have no adhesiveness to the skin, but to be used in contact with the skin so that the drugs may be contact transferred to the skin instead of sticking to the skin.

BACKGROUND OF THE ART

The development of pharmaceuticals is now undergoing various searching investigations made in the attempt to exploit novel compounds having an excellent efficacy and at the same time to further increase the efficacy of these novel chemical substances or of such chemicals that have already been in use as pharmaceuticals by changing the dosage form or by optimizing the dosage regimen.

For example, with the purpose of prolongating the duration time of medicines which have a short half-life period which is regarded as the parameter for the effective duration time of medicines in the body, there have been considerable activities to develop sustained release pharmaceuticals which are made to have a concentration between the minimum effective concentration or higher and the maximum safety concentration or lower, so that the effective ingredients may be absorbed into the human body in the whole range of effective blood concentration extending over a long period of time.

As examples of sustained release pharmaceuticals, there are pharmaceutical preparations for percutaneous administration use such as ointments and aerosols. Since these preparations are applied to the skin at a rough estimate, their dosages differ from time to time and in the case of ointments, they sometimes cause trouble to the users by smearing their clothes. Furthermore, drugs contained in an ointment are taken into the body through the skin of a user by absorption while under such influences as concentration of the drugs contained in the ointment, thickness of the applied ointment, diffusion speed of the drugs in the substrate of an ointment, and absorption speed through the skin, thus building up so many factors as to cause uncertain conditions at the time of administration, and accordingly ointments have a problem of being not satisfactorily usable as pharmaceutical preparation whose effective concentration and adverse side effects are taken into serious consideration.

With the object of curing such defects, there are tape plasters and sticking plasters which are made to contain a certain amount of drugs in their adhesive layer and to have a certain handy size (Japanese Patent Laid-Open Publication 116011/'82 and 134020/'83).

By use of tape plasters and sticking plasters, many problems which occur with the use of ointments and aerosols can be solved.

However, since tape plasters and sticking plasters are used by making the drug-containing adhesive layer stick to the skin, they often cause an inflammation of the skin where they were adhered to. There is another problem: when the used tape plasters or sticking plasters are removed for renewal, the stratum corneum which forms the skin surface is damaged and if tape plasters or sticking plasters are repeatedly applied to the same site of application as before a change in the speed of absorbing the drugs takes place.

Also, since the skin has its effect on the metabolism including the release of water, it is avoided to make the adhesion area extremely large. It has, therefore, been regarded that drugs of low percutaneous absorption rate are not suited for percutaneous administration use.

There is still another problem: these tape plasters or sticking plasters, once get wet as in case of taking a bath, become apt to fall off, and the wet plasters hardly retain their adhesiveness to the skin and have to be discarded in spite of enough residual drugs left in them.

DISCLOSURE OF THE INVENTION

As the result of intensive research conducted,
in view of the aforementioned faults, with the object of obtaining a sustained release pharmaceutical preparation which is harmless to the skin and capable of releasing a required amount of drugs for a long period of time, the present inventors have come to find that this object can be accomplished by a pharmaceutical preparation that is mainly composed of a drug layer which is made to contain drugs, to have no adhesiveness to the skin, but to be used in contact with the skin so that the drugs may be contact transferred to the skin instead of sticking to the skin, thus completing the present invention.

The present invention provides a sustained release pharmaceutical preparation for percutaneous administration use mainly composed of a drug layer which is made to contain drugs, to have no adhesiveness to the skin, but to be used in contacts with the skin.

1 ... Hollow fibers have many centrifugally extending pores.
2 ... Adhesive layer (1)
3 ... Backing material (polyethylene terephthalate film)
4 ... Adhesive layer (2)
5 ... Elastic tape
6 ... Adhesive layer (3)

Figure 2:
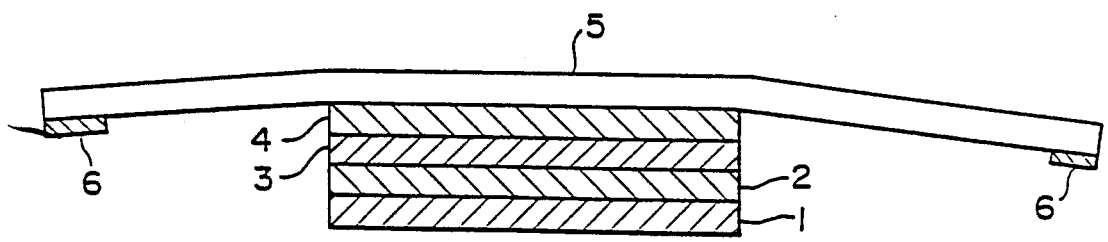

FIG. 2 is a cross sectional illustration of pharmaceutical preparation obtained in Example 2 to show a sustained release pharmaceutical preparation of this invention.

1 ... Membrane which allows the drugs to pass through.
2 ... Adhesive layer which contains the drugs (1)
3 ... Backing material
4 ... Adhesive layer (2)
5 ... Elastic tape
6 ... Adhesive layer (3)

Figure 3:
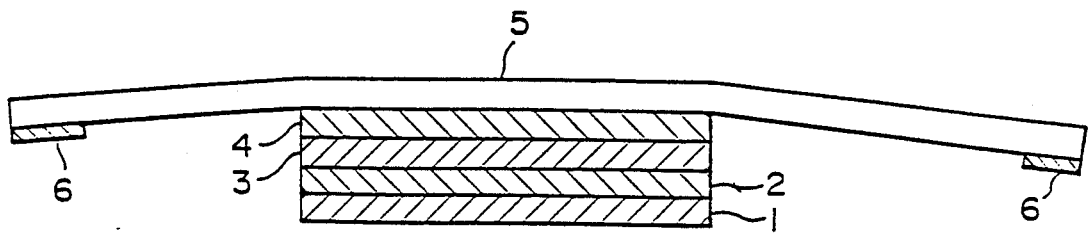

FIG. 3 is a cross sectional illustration of pharmaceutical preparation obtained in Example 3 to show a sustained release pharmaceutical preparation of this invention.

1 ... Multiporous membrane which contains the drugs.

2 ... Adheisve layer (1)
3 ... Backing material
4 ... Adhesive layer (2)
5 ... Elastic tape
6 ... Adhesive layer (3)

BEST MODE OF CARRYING OUT THE INVENTION

The first of the forms designed for the sustained release pharmaceutical preparation of the present invention is one mainly comprising a drug layer consisted of hollow fibers having many centrifugally extending pores and the drugs contained therein.

What is referred to as hollow fibers having centrifugally extending pores here desirably be such hollow fibers as those which have micropores scattered along the whole lengthwise profile and arranged to extend centrifugally, and part of them, at least, are made to open into the fibers' tubular hollows.

With regard to the cross-sectional view of the hollow fibers to be used in the present invention, no restriction is laid on their external form and the internal form. For instance, both the external and the internal may take almost circular form; any one of the external and the internal may take almost circular form and the other a modified cross-sectional form; or both the external and the internal may take a modified cross-sectional form either similar or dissimilar to each other. Also no limit is set on the size of the external.

The hollow ratio of the hollow fibers of this invention may be subject to no restriction; however, it is especially desirable to keep the ratio higher than 5%. The ratio of the centrifugally extending pores to the cross-sectional area of the fiber should preferably be in the range of 0.001 to 70%, more preferably from 0.01 to 50%, still more preferably from 1 to 50% of the cross-sectional area of the fiber except for the hollow part.

In the present invention, it is advisable to use such hollow fibers cut in length more than 10 times the diameter of the fiber. In case where the fiber is cut in length more than 10 times the diameter, the medicine filled in the tubular hollow is released much more through the centrifugally extending open pores than from the cross-sectional openings of the fiber, thus increasing the sustained release effect of the drugs desirably. Also in case where the ratio of length to diameter is 10:1 or more, the pharmaceutical preparation gives less stingy irritation to the skin of the user upon its application to the satisfaction of the user.

In the present invention it is advisable to use the hollow fibers in the state of being almost infinitely long in contrast to its diameter and also in the form of a woven, knitted, or nonwoven fabric, because, when so prepared, it comes to bear good handling, good feeling to the skin, and appropriate sustained release of drugs, thus displaying its merits to the utmost.

As the material of the hollow fibers to be used in this invention, selections may be made from among such polyesters as polyethylene terephthalate, polyvinyl chloride, and polyvinyl acetate; such polyolefins as polyethylene and polypropylene; such polyamides as nylon 6 and nylon 66; polyurethane, cellulose acetate, and polyacrylonitrile. Of these mentioned above, polyesters are desirable, especially polyethylene terephthalate is highly desirable.

The hollow fibers to be used in this invention can be manufactured according to such methods as described in Japanese Patent Laid-open Publication Nos. 20612/'81, 20613/'81, and 43420/'81.

In this invention, hollow fibers can also be used in a combination of those of different materials, forms, or hollow ratios.

In this invention, hollow fibers which, as described in the above, have many centrifugally extending pores and whose tubular hollows (tubular hollows and/or centrifugally extending pores) are made to contain drugs, are used. The drugs may be contained alone in the tubular hollows, or may be made to coexist together with any publicly known excipient, solubilizer, dispersing agent, and any kind of facient.

The drugs may be filled into the tubular hollow of a hollow fiber by any known method. For instance, a method in which the hollow fibers are immersed in a solution in which the drugs are dissolved, and taken out of the solution, followed by the removal of the solvent; or a method in which the drugs are mixed with an excipient, solubilizer, dispersing agent, percutaneous absorbefacient, then the mixture is made into a solution or a paste, and the hollow fibers are immersed in the solution or smeared with the paste, may be adopted. Such procedures as heating, application of pressure, vacuum chamber treatment, and ultrasonic vibration may also be adopted to help the drugs or mixture or drugs and additives make their way into the tubular hollows of hollow fibers.

Hollow fibers which contain the drugs can be used by applying directly to the skin or in the form of next-to-skin wear.

With the object of improving the handling, the sustained release pharmaceutical preparation of this invention may be made to have the form of a sustained release pharmaceutical preparation which comprises a drug layer consisting of hollow fibers having many pores extending centrifugally from the tubular hollows to periphery and drugs contained therein and supports which hold the drug layer in its place.

The supports are attached to the reverse side of the drug layer which comes into contact with the skin.

As the supports, a tape which is made to have adhesiveness or a non-adhesive tape which is partly made to have an adhesive layer for sticking to the skin may be mentioned. It is advisable to make the tape wholly or partly elastic and permeable.

A tape which is made to have elasticity, nonadhesiveness and permeability is especially desirable. An adhesive layer may be established on a part of the tape as a general practice to make the tape stick to the skin. Thus prepared tape allows its user to fit it around the waist, chest, leg and foot, and arm and remove it as he wishes. In case where the pharmaceutical preparation with a tape like this attached thereto is in use and the user may necessarilly take a bath or a shower, he can remove the pharmaceutical preparation and apply it again, and it may be said that the object of a sustained release effect required of the pharmaceutical preparation is fully satisfied. An adhesive or nonadhesive tape which is wholly or partly made elastic can be prepared by a singular use of publicly known elastic substance such as woven stuff, knitted fabric, sheet, and film made of rubber, urethane, and polyester, or by a combined use of woven, knitted, or nonwoven fabric made of polyethylene, polypropylene, polyester, polyamide, or cotton, and an elastic substance incorporated thereinto. When it is desired to give adhesiveness to the tape, the tape may be allowed to have a pressure sensitive adhesive applied to one side of the tape. A nonadhesive tape may be made to have an adhesive layer formed on a part of the tape to stick to the skin.

As for the adhesives to be used here, ordinary pressure sensitive adhesives are used. For example, viscous compounds of rubber type such as silicone rubber, polyisoprene rubber, styrene-butadiene copolymerized rubber, acrylic rubber, and natural rubber; viscous compounds of vinyl type such as polyvinyl alcohol and ethylene-vinyl acetate copolymer; viscous compounds mainly comprising silicone adhesive, polyurethane elastic body, polyester elastic body, and polybutadiene elastic body; and acrylic resins provide a range of selection.

As the backing materials, sheets or films made from polyethylene terephthalate, cellulose acetate, ethyl cellulose, cellophane, vinyl acetate-vinyl chloride copolymer, polyamide, polyethylene and polyvinylidene chloride may be mentioned.

The aforementioned adhesive layer and backing material may be established in two or more layers if so required.

The second of the forms designed for the sustained release pharmaceutical preparation of the present invention is one mainly comprising a drug layer consisting of an adhesive layer which contains the drugs and a nonadhesive layer which comes into contact with the skin and allows the drugs to pass through, and a support which hold them in their place.

As the adhesives to be used here, the ordinary pressure sensitive adhesives as mentioned in the above may be mentioned. For example, viscous compounds of rubber type such as silicone rubber, polyisoprene rubber, styrene-butadiene copolymerized rubber, acrylic rubber, and natural rubber; viscous compounds of vinyl type such as polyvinyl alcohol and ethylene-vinyl acetate copolymer; viscous compounds mainly comprising silicone adhesive, polyurethane elastic body, polyester elastic body, and polybutadiene elastic body; and acrylic resins such as n-butylacrylate, n-butylmethacrylate, hexylacrylate, 2-ethylbutylacrylate, 2-ethylhexylacrylate, and 2-ethylhexylmethacrylate may be mentioned for selection.

In the present invention, the adhesive layer is made to contain drugs by any method chosen at discretion, and furthermore, a non adhesive layer, which allows the drugs to permeate through the layer and does not stick to the skin, is established in order to prevent said adhesive layer from sticking to the skin.

As for the methods for making the adhesive layer contain the drugs, there are, for instance, a method in which drugs are dissolved in a solution of adhesive such as methanol, ethanol, acetone, and ether, and a method in which drugs are dissolved in a solvent such as methanol, ethanol, acetone, and ether, and then an adehsive is immersed in the obtained solution.

It is usual to prepare an adhesive layer to a thickness of 5 to 1,000 microns, preferably 10 to 500 microns.

As the nonadhesive layer which allows the drugs to permeate therethrough and do not stick to the skin, ethylene-vinyl acetate copolymer film, polyurethane film, polyethylene multiporous film, nonwoven fabric, and knitted fabric, for instance, may be mentioned.

It is desirable to keep the thickness of a nonadhesive layer usually in the range of 0.1 to 300 microns.

In case where the drug-containing adhesive layer has no adhesiveness to the skin, it is not necessary to cover its surface with a nonadhesive layer; however, the sustained release effect of the drugs can be increased by establishing a nonadhesive layer.

A support is established on the drug layer thus obtained. As the support, the aforementioned adhesive tapes or nonadhesive tapes, part of which is made to have an adhesive layer for sticking to the skin, can be used alike.

An adhesive layer and backing material can also be set between the drug layer and the support, if necessary, being made of the same matefials as described before.

The third of the forms designed for the sustained release pharmaceutical preparation of the present invention is one mainly comprising a drug layer, which consists of a porous layer containing drugs and a nonadhesive layer established on the side of the porous layer which comes into contact with the skin when the porous layer is adhesive, and a support which holds the drug layer on.

As the porous layer, film, sheet, nonwoven fabric, woven fabric, and knitted fabric, with pores having a diameter of $0.001 \sim 50\mu$, made from polyolefin such as polyethylene and polypropylene; polyester; polyamide, polyurethane; polyvinyl alcohol; cellulose; cellulose acetate; vinyl chloride; or fluorine-contained resin may be used solely or in combination.

As for the methods for making the porous layer contain the drugs, there are, for instance, a method in which the drugs are dissolved in a solution of methanol, ethanol, acetone, or ether and then the porous layer is immersed in thus obtained solution and a method in which the drugs are mixed with such ordinarily used additives as excipient, solubilizer, dispersing agent, and percutaneous absorbefacient, the mixture is made into a solution or ointment, and then the porous layer is immersed in the solution or smeared with the ointment.

In case the drug-containing porous layer has adhesiveness, such a nonadhesive layer that allows the drugs to permeate through as mentioned before is to be established on the surface of the layer which is to come into contact with the skin. The same materials and the methods of preparing the nonadhesive layer as described hereinbefore may also be adopted here again.

As for the support to be established on the drug layer comprising a porous layer, the same support as described before may also be established here in the same way.

Furthermore, a backing material and/or adhesive layer may be established between the drug layer and the support, if necessary. The same backing material and adhesive layer as mentioned above may be mentioned for use in this case.

These three forms are given in the above as typical ones for making the sustained release pharmaceutical preparation of this invention and these three forms may also be utilized in any combination, if required. The size, or area, of the pharmaceutical preparation of this invention may very freely in the range of 1 $cm^2$ to 6 $m^2$ depending upon the kind of the drug and when the drug has poor percutaneous absorptive action or has high effective blood concentration, its area can be made larger.

As the drugs which can be used in the present invention, the following may be mentioned.

(1) Vasodilators for coronary vessel such as nitroglycerin, 1,2,3-propanetriolmononitrate, 1,2,3-propanetrioldinitrate, and their ester derivatives, isosorbide dinitrate, isosorbide-5-mononitrate, pentaerythritol tetranitrate, papaverine hydrochloride, hepronicate, molsidomine, nicomol, simfibrate, diltiazem hydrochloride, cinnarizine, dipyridamole, trapidil, trimetazidine hydrochloride, carbocromene, prenylamine lactate, and dilazep dihydrochloride;

(2) Antiarrhythmic agents or stenocardiac drugs such as pindolol, disopyramide, bupranolol hydrochloride, trichlormethiazide, furosemide, prazosin hydrochloride, metoprolol tartrate, carteolol hydrochloride, oxprenolol hydrochloride, and propranolol hydrochloride;

(3) Antihypertensive agents such as ecarazine hydrochloride and hydrolazine hydrochloride;

(4) Cardiotonics such as metildigoxin, caffeine and sodium benzoate, caffeine, dopamine hydrochloride, dobutamine hydrochloride, octopamine hydrochloride, diprophylline, ubidecarenon, digitalis, and digoxin;

(5) Drugs for bronchial asthma such as procaterol hydrochloride, pirubuterol hydrochloride, clofedanol hydrochloride, salbutamol sulfate, trimetoquinol hydrochloride, bitolterol mesilate, isoproterenol, isoaminil citrate, carbocisteine, tranilast and theophylline;

(6) Antihypertensive or Ca antagonists such as clonidine, nifedipine, nicardipine, and verapamil;

(7) Antiphlogistics and dermatological agents such as aspirin, salicyclic acid, methyl salicylate, ethyl salicylate, choline salicylate, sodium salicylate, salicylosalicyclic acid, salicylamide, glycol salicylate, (-menthol, aminopyrine, antipyrine, clofezone, ketophenylbutazone, camphor, mentha oil, thymol, isopropylantipyrine, phenylbutazone, feprazone, benzyl nicotinate ester, capsicum extract, capsaicin, acetaminophen, oxyphenbutazone, pentazocine, eptazocine, diffunisal, phenazole, mepirizole, piroxicam, benzydamine, phenacetin, tiaramide, bufexamac, flufenamic acid, aluminum flufenamate, indometacin, tramdol hydrochloride, ibuprofen, alclofenac, acemetacin, sulpyrine, guaiazulene, ketoprofen, flurbiprofen, diclofenac sodium, fenaprofen, naproxen, clidanac, sulindac, benoxabrofen, indoprofen, mefenamic acid, tolmetin, metiazinic acid, protizinic acid, perixazole citrate, pranoprofen, fenbufen, fentizac, tiaprofenic acid, tinoridine hydrochloride, zomepirac, pimeprofen, bendazac, fenoprofen calcium, prednisolone, amphenac sodium and their derivatives;

(8) Local anesthetics such as lidocaine, benzocaine, ethyl aminobenzoate, procaine hydrochloride, dibucaine, and procaine;

(9) Hypotensive diuretics such as mefruside, penflutizide, bumetamide, hydrothiazide, bentroflumethiazide, and reserpine.

(10) Hypnotics and sedatives such as methaqualone, glutethimide, flurazepam, bromovaleryurea, flurazepam hydrochloride, haloxazolam, triazolam, phenobarbital, chloral hydrate, nimetazepam, and estazolam;

(11) Central nervous system agents such as levodopa, fluphenazine, flutazolam, phenobarbital, phenobarbital sodium, methylphenobarbital, thioridazine, diazepam, benzbromarone, clocapramine hydrochloride, clotiazepam, chlorpromazine, haloperidol, and lithium carbonate;

(12) Psychoanaleptics such as 3-(2-aminobutyl) indole acetate;

(13) Adrenocortical hormones such as epinephrine, cortisone acetate, hydrocortisone acetate, hydrocortisone, predonisolone, sodium hydrocortisone succinate, triamcinolone acetonide, triamcinolone diacetate, dexamethasone phosphosic ester, methylpredon:solone, dichlorison acetate, methylpredonisolone acetate, fluocinolone acetonide, dexamethasone acetate, dexamethasone, sodium dexamethasone sulfate, sodium dexamethasone phosphate, paramethasone acetate, fluorometholone, estrone, betamethasone sodium phosphate, betamethasone, betamethasone valerate, flumethasone pivalate, beclometasone propionate, fludroxycortide, hydrocortisone butyrate, betamethasone dipropionate, clobetasol propionate, difluocortolone pivalate, halcinonide, prednisolone pivalate, and hydrocortisone butylate propionate;

(14) Antitubercular agents such as sulfa drugs like sulfadimethoxine, sulfisoxazole, and sulfisomidine; ethambutor hydrochloride, isoniazid, and calcium paraaminosalicylate;

(15) Antihistamic and antiallergic agents such as homochlorcyclizine hydrochloride, diphenhydramine hydrochloride, chlorpheniramine, diphenylimidazole, chlorpheniramine maleate, glycyrrhetic acid, tranilast, and ketotifen;

(16) Drugs for myasthenia such as pyridostigmine bromide;

(17) Drugs for post-cerebral embolism such as nicardipine hydrochloride, cinepazide maleate, pentoxifylline, and ifenprodil tartrate;

(18) Antibiotic drugs such as penicillin, tetracycline, oxytetracycline, chlortetracycline, chloramphenicol, sulfonamide, talampicillin hydrochloride, fradiomycin sulfate, erythromycin, tetracycline hydrochloride, bacampicillin hydrochloride, fradiomycin, leucomycine, cefroxadine, cephalosporin, ampicillin, cephradine, cefalexin, cefaclor, neomyqin sulfate, bacitracin, cepholothin sodium, kanamycin sulfate, fosfomycin calcium, streptomycin, gentamicin sulphate, fradiomycin sulphate, gramicidin S, mikamycin, and colistin;

(19) Antibacterial and antifungal agents such as iodine, povidon iodine, boric acid, sodium borate, oxydale, potassium permanganate, ethanol, isopropanol, formaline, cresol, dimazole dihydrochloride, siccanin, phenyliodoundecynoate, hexachlorophene, creosote, resorcin, acrinol, methylrosanilinium chloride, benzethonin chloride, sodium lauryl sulfate, mercuric chloride, meclosorb (meclocycline), mercurochrome, chlorhexidine gluconate, alkylpolyaminoethylglycine hydrochloride, benzalkonium chloride, nitrofurazone, nystatin, acesulfamin, clotrimazole, sulfamethizole, tolnaftate, pentamycin, amphotericin B, pyrrolnitrin, undecylenic acid, miconazole, trichomycin, variotin, haloprogin, and dimazole hydrochloride;

(20) Keratolytics such as pine tar and chrysarobin;

(21) Antiepileptics such as primidone, valproate sodium, nitrasepam, meprobamate, and clonazepam;

(22) Antineoplastic agents such as bleomycin, aclacinomycin, adriamycin, carmofur, pipobroman, melphalan, carboquone, thioinosine, tamoxifen citrate, peplomycin, tegafur, 5-fluorouracil and its derivatives, and mitomycin;

(23) Sex hormones such as progesterone, hydrooxyprogesteron oxyprogesterone caproate, hydroxyprogesterone acetate, testosterone, testosterone enanthate, chlormadinone acetate, methyltestosterone, dimethisterone, norethisterone, mestranol, estriol, estriol benzoate, estriol tripropionate, estradiol valerate, gestonorone caproate, fluoxymesterone, cyproterone acetate, danazol, mepitiostane, epitiostanol, dinoprost tromethamine, dinoprost, bromocriptine mesilate, and estrone;

(24) Vitamins such as pyridoxine hydrochloride, cobamamide, nicotinamide, pantethein, calcium pantothenate, flavin adenine dinucleotide, folic acid, pyridoxal phosphate, ascorbic acid, vitamin A, vitamin D, vitamin E, ergocalciferol, alfacarcidol, cholecalciferol, 1,25-dihydroxy vitamin $D_3$, 1,24-dihydroxy vitamin $D_3$, octothiamine, riboflavin, and riboflavin tetrabutyrate;

(25) Antitussives and expectorants such as hexoprenaline sulfate, salbutamol sulfate, powdered opium, ethylmorphine hydrochloride, morphine hydrochloride, opium alkaloids hydrochloride, fentanyl citrate, pethidine hydrochloride, codein phosphate, dihydrocodeine phosphate, and bisolvon;

(26) Antiphlogistic enzymes such as lysozyme, etc.

(27) Drugs for hepatic diseases such as asparaginate, orotic acid glucuronolactone, thioctic acid amide and sodium protoporphyrin;

(28) Antidotes such as glutathione;

(29) Drugs for diabetes mellitus such as insulin, glibenclamid, and glymidine sodium;

(30) Drugs for constipation such as picosulfate sodium, dantrolene sodium, sennoside A·B calcium salt, and cascara sagrada liquid extract;

(31) Immuno modulators such as D-penicillamine, bestatin, levamisole, and platonin;

(32) Drugs for cystitis, chronic cystitis, and urethritis such as carindacillin sodium, carfecillin sodium, enoxacin, cefadroxil, hexamine mandelate, nitrofurantoin, ergometrine maleate, methylergometrine maleate, sparteine sulfate, dinoprost, dinoprost tromethamine, dinoproston, pimaricin, miconazole nitrate, econazole nitrate, tribenoside, and flavoxate hydrochloride;

(33) Ophthalmic remedies such as timolol maleate and catalin;

(34) Antiulcer agents such as aceglutamide aluminum, cetraxate hydrochlolide, pirenzepine hydrochloride, cimetidine, L-glutamine, and gefarnate;

(35) Drugs for arteriosclerosis such as clinofibrate, elastase, simfibrate, bencyclane fumarate, and niceritrol;

(36) Drugs for suppurative diseases such as sulfadiazine silver, gentamicin sulfate, and mafenide acetate;

(37) Drugs for parasitic cutaneous diseases such as exalamide.

These medicines mentioned above are used singly or as a mixture of more than one properly chosen.

As the drugs to be used here, vasodilators for coronary vessel, antiarrhythmic agents, stenocardiac drugs, cardiotonics, and antihypertensive agents are very desirable and the vasodilators for coronary vessel are especially desirable. The amounts of the drugs to be used may be properly decided depending upon the pharmacological potency and the absorptivity to the skin of the drug.

The pharmaceutical preparation of this invention may be allowed to contain an absorbefacient, solubilizer, dispersing agent, filling material, etc.

As the absorbefacient or dispersing agent, such surface active agents as sodium lauryl sulfate, sodium dodecylbenzene sulfonate, sodium alkyldiphenyl ether difulfonate, dioctyl sodium sulfosuccinate, and polyoxyalkylphenyl ether sulfate ammonium salt; such alcohols as ethanol, glycerin, diethylene glycol, propylene glycol, polyethylene glycol, and higher fatty acid alcohol; dimethyl sulfoxide and alkylmethyl derivatives; salicylic acid, urea, dimethylacetamide, diethyl toluamide, dimethylformamide, dioctyl sebacate, lanolin, allantoin, squalene, carbopol, diisopropyl adipate, pyroglutamic acid lauryl ester, ethyl laurate, methyl nicotinate, sorbitol, pyrrolidone derivatives like dodecyl pyrrolidone and methyl pyrrolidone, olive oil, castor oil, liquid paraffin, vaseline, gelatin, amino acid, benzyl nicotinate, (-menthol, camphor, and dodecylazacycloheptane-2-one, for instance, may be used.

As the filling materials, water, titanium oxide, calcium carbonate, carbon black, red ion oxide, dyes and pigments, liquid paraffin, vaseline, lactose, perfume, deodorant, powders or moldings of synthetic resin such as polyethylene, polypropylene, polyester, and polystyrene may be mentioned.

Also it is advisable to use highly water absorption polymers such as hyaluronic acid and polyacrylic soda as the additives in combination with the aforementioned excipients, because such additives absorb the moisture of sweats, etc. from the skin to keep the surface, which is in contact with the skin, of the pharmaceutical preparation moist, thus improving the absorption of the drugs from the skin.

As explained in detail in the above, the pharmaceutical preparation of this invention is made to transfer the drugs to the skin while it is kept in contact with the skin instead of adhering to the skin and has much improved the defects of those conventionally used tape plasters and sticking plasters and has also increased its sustained release effect of the drugs.

The following examples will further serve to illustrate the present invention. All parts in the examples are by weight unless otherwise indicated and the hollow fibers and adhesive solutions used in the examples are prepared according to the methods described below.

(1) Hollow fiber speciment 297 parts of dimethyl terephthalate, 265 parts of ethylene glycol, 53 parts of 3,5-di (carbomethoxy)sodium benzenesulfonate (11.7 mole % to dimethyl terephthalate), 0.084 parts of manganese acetate tetrahydrate, and 1.22 parts of sodium acetate trihydrate were placed in a glass flask equipped with a rectification column and subjected to the ester interchange reaction according to an ordinary method. After the theoretical amount of methanol was distilled away, the reaction product was put in a polycondensation flask equipped with a rectification column together with 0.090 part of 56% phosphoric acid aqueous solution as the stabilizer and 0.135 part of antimony trioxide as the catalyst. The reaction was carried out at 275° C. at ordinary pressure for 20 minutes and under reduced pressure of 30 mmHg for 15 minutes, and lastly under high vacuum for 100 minutes, the final for 15 minutes, the final internal pressure being 0.38 mmHg to give a copolymer having a limiting viscosity number of 0.405 and a softening point of 200° C. After the reaction was over, the obtained copolymer was formed into chips according to the generally practised method.

15 parts of thus obtained copolymer chips and 85 parts of polyethylene terephthalate chips having a limiting viscosity number of 0.640 were mixed for 5 minutes in a NAUTA mixer (Hosokawa Iron Works) and were then dried in the stream of nitrogen at 110° C. for 2 hours and further at 150° C. for 7 hours. Thereafter, the mixed chips were melt-kneaded at 290° C. by use of a double screw extruder to give chips. The chips had a limiting viscosity number of 0.520 and a softening point of 262° C.

After thus prepared chips were dried according to the ordinary method, they were spun by use of a spinneret with circular slits, each having a width of 0.05 mm and a diameter of 0.6 mm, which were closed at two points to form circular arc openings, according to an ordinary method to give hollow fibers (void ratio 25%)

having a ratio of 2:1 between the outside diameter and the inside diameter. Thus obtained raw fibers were 300 denier/24 filaments. These raw fibers were drawn by a drawing factor of 4.2 according to the ordinary method to obtain multifilament yarns of 71 denier/24 filaments. A knitted fabric was made of these multifilament yarns and was scoured according to the ordinary procedure, dried, and treated in 1% caustic soda aqueous solution at a boiling temperature for 2 hours to obtain a fabric having an alkaline cleaning loss in weight of 15%, water absorption rate (determined as per JIS-L 1018) of 3 seconds and water absorption degree of 80%.

Thus obtained hollow fiber was one that had micropores scattered all over its outer surface. These pores, part of which reach the tubular hollow of the fiber, are arranged extending centrifugally on the fiber's profile.

The water absorption degree was determined by the following method. The specimens obtained from a dried fabric were immersed in water for 30 minutes or more and then dehydrated for 5 minutes in the hydroextractor of a home electric washing machine. The water absorption degree was calculated from the weight of the dry specimen and the weight of the specimen after dehydration by the following formular:

$$\text{Water absorption degree} = \frac{\left(\begin{array}{c}\text{Weight of the}\\\text{specimen after}\\\text{dehydration}\end{array}\right) - \left(\begin{array}{c}\text{Weight of}\\\text{the dry}\\\text{specimen}\end{array}\right)}{(\text{Weight of the dry specimen})} \,(\%)$$

(2) Adhesive solution

A reaction vessel equipped with a reflux condenser and an agitator was fed with 97.4 parts of 2-ethylhexyl acrylate, 2.5 parts of methacrylic acid, 0.1 part of polyethylene glycol (polymerization degree 14) dimethacrylate, 1.0 part of benzoyl peroxide, and 100 parts of ethyl acetate and the polymerization was carried out in the atmosphere of nitrogen at 60° C. for 9 hours with slow stirring. The polymerization conversion rate was 99.9%.

500 parts of ethyl acetate was added to the obtained polymeric solution to adjust its solid substance concentration to about 20%.

Example 1

After 10 parts of the hollow fiber specimen was immersed in 100 parts of an acetone solution containing 50 parts of isosorbid dinitrate kept in a vessel, the specimen was taken out and air-dried.

On the other hand, the adhesive solution was coated on a polyethylene terephthalate film having a thickness of 5 μ and the adhesive layer wa made to attain a thickness of 10 μ after drying.

The isosorbid dinitrate-containing hollow fiber specimen prepared in the above was spread on the adhesive layer and the hollow fiber specimen had its surface pressed lightly with a pressure roller to be adhered to the adhesive layer.

Figure 1:
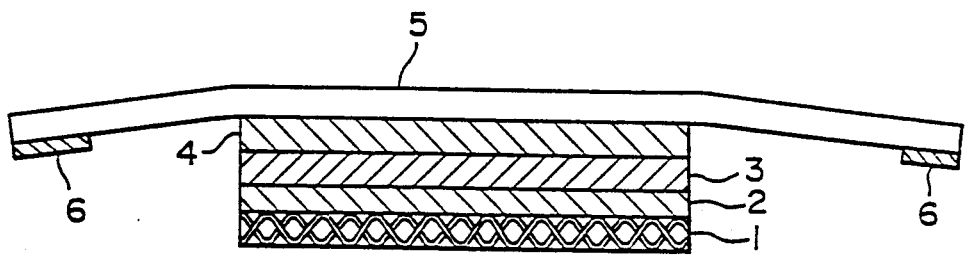
FIG. 1 is a cross sectional illustration of a pharmaceutical preparation obtained in Example 1 to show a sustained release pharmaceutical preparation of this invention.

The isosorbid dinitrate-containing hollow fiber specimen thus backlined with a polyethylene terephthalate film was cut to give a piece of 5 cm×4 cm. This was applied to the depilated back of a rabbit weighing 3.0 kg in such a way as to make the hollow fiber come into direct contact with the exposed skin of the rabbit and was kept in place under light pressure of elastic tapes applied thereto (in this case the applied pharmaceutical preparation is one as shown in FIG. 1). At the predetermined times, the blood was taken from the rabbit to determine the concentration of the drug in the blood. The appearance on the skin (skin irritability) was also examined.

The result is shown in Table 1.

The aforementioned blood concentration was performed by the following method. After the crystal was separated from 3 ml of the collected blood, it was extracted with 4 ml of n-hexane and concentrated. Ethyl acetate was added to the concentrate to make a total of 100 μl, and the determination was conducted by GC-ECD.

EXAMPLE 2

An adhesive solution, which contained 10 parts of isosorbid dinitrate against 100 parts of the solid matters dissolved therein, was applied to the surface of a 5 μ-thick polyethylene terephthalate film (backing material) in such a way as to make a 50 μ-thick adhesive layer after drying.

A 40 μ-thick ethylene-vinyl acetate (EVA) film (drug-permeable film) was applied to one side of the aforementioned adhesive layer under pressure. The obtained laminate was cut to give a piece of 5 cm×4 cm. This was put on the depilated back of a rabbit weighing 2.8 kg in such a way as to make its EVA side come into contact with the skin of the rabbit. The piece of laminate was kept in contact to the place of application by use of elastic tapes (in this case the applied pharmaceutical preparation is one as shown in FIG. 2). The blood was taken from the rabbit at several predetermined times to measure the blood concentration of the drug. The appearance on the skin (skin irritability) was also examined.

The result is shown in Table 1.

EXAMPLE 3

A polypropylene film containing isosorbid dinitrate was prepared by applying 50 parts of acetone solution containing 25 parts of isosorbid dinitrate dropwise to 1,000 parts of 25 μ-thick porous polypropylene film having an average pore diameter of 0.1 μ (Duragard made by Polyplastics Co., Ltd.) followed by air drying.

Apart from the above procedure, an adhesive terephthalate film to form an adhesive layer having a thickness of 10 μ after drying.

The isosorbid dinitrate-containing polypropylene film was spread over the adhesive layer and pressed lightly with a pressure roller to be stuck to the adhesive layer.

Thus obtained laminate was cut to give a piece of 8 cm×5 cm. This was placed on the depilated back of a rabbit having a weight of 3.1 kg with its polypropylene film side touching the skin of the rabbit and fixed lightly to its place with elastic tapes (in this case the applied pharmaceutical preparation is one shown in FIG. 3). The blood was taken from the rabbit at the scheduled times to determine the blood concentration of the drug. Also, the appearance on the skin (skin irritability) was examined.

The result is shown in Table 1.

REFERENCE EXAMPLE 1

An adhesive solution, which contained 10 parts of isosorbid dinitrate against 10 parts of the solid matters dissolved therein, was coated on a 40 μ-thick ethylenevinyl acetate a thickness of 50 μ might be formed upon drying.

In another procedure, the adhesive solution was applied to a 5 μ-thick polyethylene terephthalate film to form an adhesive layer having a thickness of 10 μ after drying. The laminate (I) prepared in the above paragraph comprising an ethylene-vinyl acetate copolymer film and an isosorbid dinitrate-containing adhesive layer was placed on the 10 μ-thick adhesive layer in such a way as to make it contact the ethylenevinyl acetate copolymer film side. Thus obtained laminate (II) was cut to give a piece of 2 cm×4 cm. This was applied to the depilated back of a rabbit weighing 2.6 kg with its isosobid dinitrate-containing side toughing the skin of the rabbit. At several predetermined times, the blood was taken from the rabbit to determine the concentration of the drug in the blood and the state of the skin was also inspected. The result in shown in Table 1.

The pharmaceutical preparation made in this Reference Example was seen partly carrying keratin of the skin when it was removed from the site of application and it could not be used repeatedly.

TABLE 1

Concentration of isosorbid dinitrate in the rabbit blood and skin irritability (unit:ng/ml)

| | Application time (hr) | | | | | | Skin |
|---|---|---|---|---|---|---|---|
| | 1 | 3 | 6 | 12 | 24 | 48 | 72 | irritability |
| Example 1 | 3.8 | 6.5 | 7.2 | 6.1 | 6.9 | 7.1 | 6.5 | No stigma found |
| 2 | 4.2 | 4.8 | 5.2 | 4.7 | 4.9 | 4.1 | 3.6 | No stigma found |
| 3 | 4.6 | 5.1 | 4.6 | 4.5 | 3.3 | 2.5 | 2.8 | No stigma found |
| Reference Example 1 | 6.1 | 6.2 | 6.4 | 5.9 | 3.7 | 1.8 | 0.6 | Stigmas were found on the skin contacting the edge of the film attached. |

INDUSTRIAL APPLICATIONS

The present invention relates to a sustained release pharmaceutical preparation for percutaneous administration use mainly composed of a drug layer which is made to contain drugs, to have no adhesiveness to the skin, but to be used in contact with the skin. It causes no harm to the skin and yet has an effect of realizing administration of a desired amount of drugs over a long period of time by slow degrees.

Therefore, the sustained release pharmaceutical preparation of this invention can be utilized for curing various diseases.

We claim:

1. A sustained release pharmaceutical preparation for percutaneous administration comprising:
   a support and
   a drug layer provided on said support, said drug layer having no adhesiveness to skin and comprising
   (a) a knitted fabric of hollow porous fibers of polyethylene terephthalate wherein the pores pass centrifugally from the wall of a tubular hollow to the peripheral surface of said fibers, and
   (b) drugs.

2. The sustained release pharmaceutical preparation according to claim 1, wherein said support is an adhesive tape or a nonadhesive tape, on part of which an adhesive layer is established to make said support stick to the skin.

3. The sustained release pharmaceutical preparation according to claim 1 or claim 2, wherein said drugs are vasodilators for coronary vessel, antiarrhytmic agents, stenocardiac drugs, cardiotonics, or anti-hypertensive agents.

* * * * *